United States Patent [19]

Malmros et al.

[11] Patent Number: 5,108,576
[45] Date of Patent: Apr. 28, 1992

[54] PYROELECTRIC THERMOMETRIC DEVICE

[75] Inventors: Mark K. Malmros, Newton; Julian Gulbinski, III, Jamison, both of Pa.; William S. Collins, San Diego, Calif.; William Gibbs, Morrisville, Pa.

[73] Assignee: Ohmicron Corporation, Newtown, Pa.

[21] Appl. No.: 206,875

[22] Filed: Jun. 13, 1988

[51] Int. Cl.$^5$ ............................................. G01N 25/48
[52] U.S. Cl. .................................. 204/403; 204/153.12; 435/180; 435/181; 435/4; 435/14; 435/288; 435/291; 436/149; 436/150; 436/151; 436/532
[58] Field of Search ............... 435/180, 181, 4, 14, 435/288, 291; 436/149, 150, 151, 532; 204/153.12, 403

[56] References Cited

U.S. PATENT DOCUMENTS

| | | | |
|---|---|---|---|
| 3,744,296 | 7/1973 | Beltzer | 73/23 |
| 3,878,049 | 4/1975 | Tannenbaum et al. | 204/153.12 X |
| 4,560,534 | 12/1985 | Kung et al. | 422/68 |
| 4,829,003 | 5/1989 | Arney | 435/283 |
| 4,916,075 | 4/1990 | Malmros et al. | 435/291 |
| 4,935,345 | 6/1990 | Guilbeau et al. | 435/14 |

Primary Examiner—John F. Niebling
Assistant Examiner—Arun S. Phasge
Attorney, Agent, or Firm—Omri M. Behr

[57] ABSTRACT

A device for detecting the presence of a predetermined reactant in a fluid suspected of containing the same which comprises a pyroelectric film having a first and a second surface, a first electrode in contact with a portion of the first surface of said pyroelectric film, a second electrode in contact with a portion of the first surface of said pyroelectric film, said first and said second electrodes being proximate to but electrically insulated from each other, an infra-red transparent third electrode having a first and second surface, said first surface being in contact with the second surface of said film, methods of making such a device and methods of utilizing same.

30 Claims, 3 Drawing Sheets

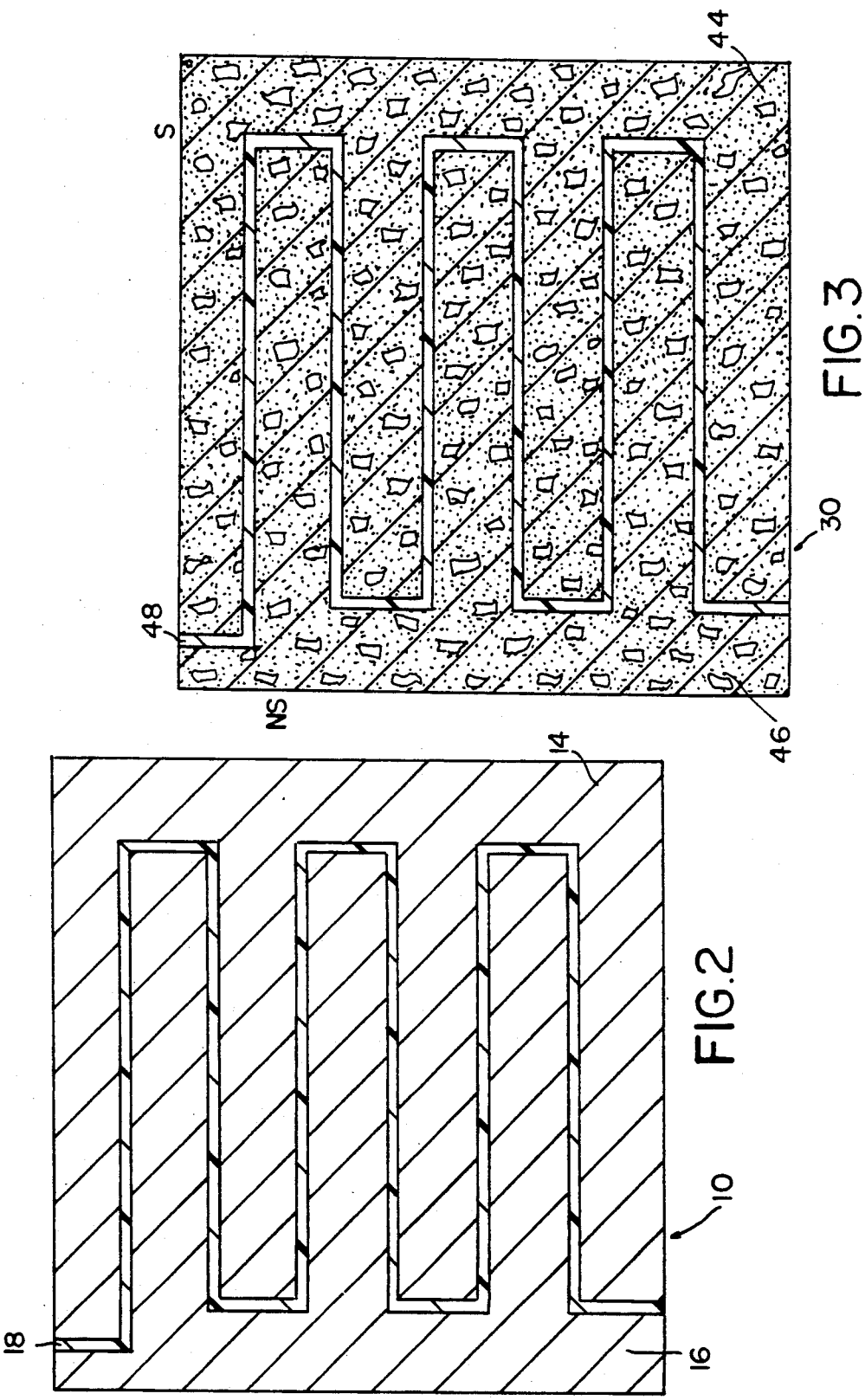

PYROELECTRIC THERMOMETRIC DEVICE

BACKGROUND OF THE INVENTION

This invention relates to methods of analytical chemistry and biochemistry that are used to determine the presence and amount of specific substances from a variety of sources. For example, in some instances, a specific protein molecule with catalytic properties, such as an enzyme, can be used for the determination of glucose, a simple sugar. Using the enzyme glucose oxidase, glucose is converted to gluconic acid and hydrogen peroxide quantitatively. The amount of hydrogen peroxide generated is then measured directly or is coupled to other quantitative methods for its determination. A variety of enzyme based analytical methods are well known and are described in the general literature.

Also of value is the use of immuno-chemical methods. Because of their specificity, antibodies can be made to a large variety of substances. These antibodies are able to bind specifically to those substances, termed antigens. This antigen-antibody binding reaction can then be used to test for the presence of that specific analyte in various samples suspected of containing the analyte.

This basic immunological procedure forms the basis for radioimmunoassay, enzyme immunoassay, fluorescence immunoassay and similar techniques.

It would be desirable to provide a device that can be used in various analytical procedures based on the thermometric responses of pyroelectric materials, where a control or reference determination can be made within the same apparatus that is used for the sample determination, improving upon the assurance that the conditions for both the sample and the control are otherwise identical and thus improving upon the accuracy of the particular determination.

SUMMARY OF THE INVENTION

Certain materials can be made to display a pyroelectric property, pyroelectricity being defined as the electric polarization induced by thermal absorption in crystals, the polarization being proportional to the thermal change. In the pyroelectric response, the film will develop a charge (and thus a potential) proportional to the rate of change of temperature across the film.

A pyroelectric thin polymer film, such as polyvinylidene fluoride (PVDF) is commercially available under the trade name Piezofilm from Pennwalt Corporation, King of Prussia, Pa.) PVDF films can be polarized in an electric field and then coated with a conducting metal film such as nickel, aluminum, palladium, etc. The resulting metallized PVDF film displays a high piezo- and pyroelectric coefficient. Such films can be configured, for the determination of heats of catalytic enzyme reactions, as a differential sensor device.

By appropriately etching the metal film into electrode areas, or elements, a differential sensor element can be made to which subsequent chemistries can be immobilized. This can be accomplished by a number of methods that allow for differential immobilization over the respective electrode area or elements.

The use of a spin coated amine derivatized epoxy film is one means of providing a chemically reactive surface that is uniform and to which proteins, such as enzymes and antibodies can be coupled using photochemically reactive coupling reagents.

In another surface coating method the metal layer is oxidized and selected reagents are coupled to the oxide. These films can be modified for differential coupling by various means well known in the art including photochemical techniques.

A preferred method of reagent immobilization for proteins is the controlled electrochemical polymerization of various monomer solutions directly incorporating the appropriate protein (such as an enzyme or antibody into the film) by cross-linking with the monomer during the electro-polymerization reaction to the respective, etched, electrode patterns.

The device may be utilized to detect the presence of the suspected analyte in one of two modes designated arbitrarily the active mode and the passive mode.

The active mode depends upon the actual measurement of caloric change which occurs during a reaction and the other depends upon the change in the thermal conductivity of a surface layer after reaction has occurred.

In the active mode, a small amount of a solution containing the suspected analyte is placed upon the upper surface of the electrode film which may, but in this mode need not be infra red transparent, which has been partially coated with reactant (which should be and generally, normally is infra red transparent) specific reagent and partially with reactant-nonspecific reagent. If the suspected analyte is present, the heat of reaction with the aforesaid two reagents, whether endothermic or exothermic, will be different. The difference in heat generated (or abstracted) in this step will be converted into electrical charge impulses by the pyroelectric film, detected by the appropriate segments of the detector electrode to provide differential signals which are amplified by the differential amplifier and then read by the conventional output.

In a passive mode, the suspected analyte is similarly placed upon the upper surface of the IRT (infra red transparent) electrode, allowed to react and the analyte solution washed off and the upper surface dried. The washing and drying steps are not absolutely necessary, however, taking this approach gives rise to more reproducible results. The upper surface is then irradiated with infrared radiation and, in accordance with the steps described hereinabove, the difference in the thermal conductivity of the two segments is measured by reference to electrical signals generated thereby.

It has been found desirable to carry out this infrared radiation step utilizing very short impulses of known intensity and very short time duration.

BRIEF DESCRIPTION OF THE DRAWINGS

FIG. 2 is a downward plan view of the detector electrode segment of the present invention, and FIG. 3 is a downward plan view of the reactant-reactive sector of the present invention.

DETAILED DESCRIPTION OF THE DRAWINGS

Figure 1:
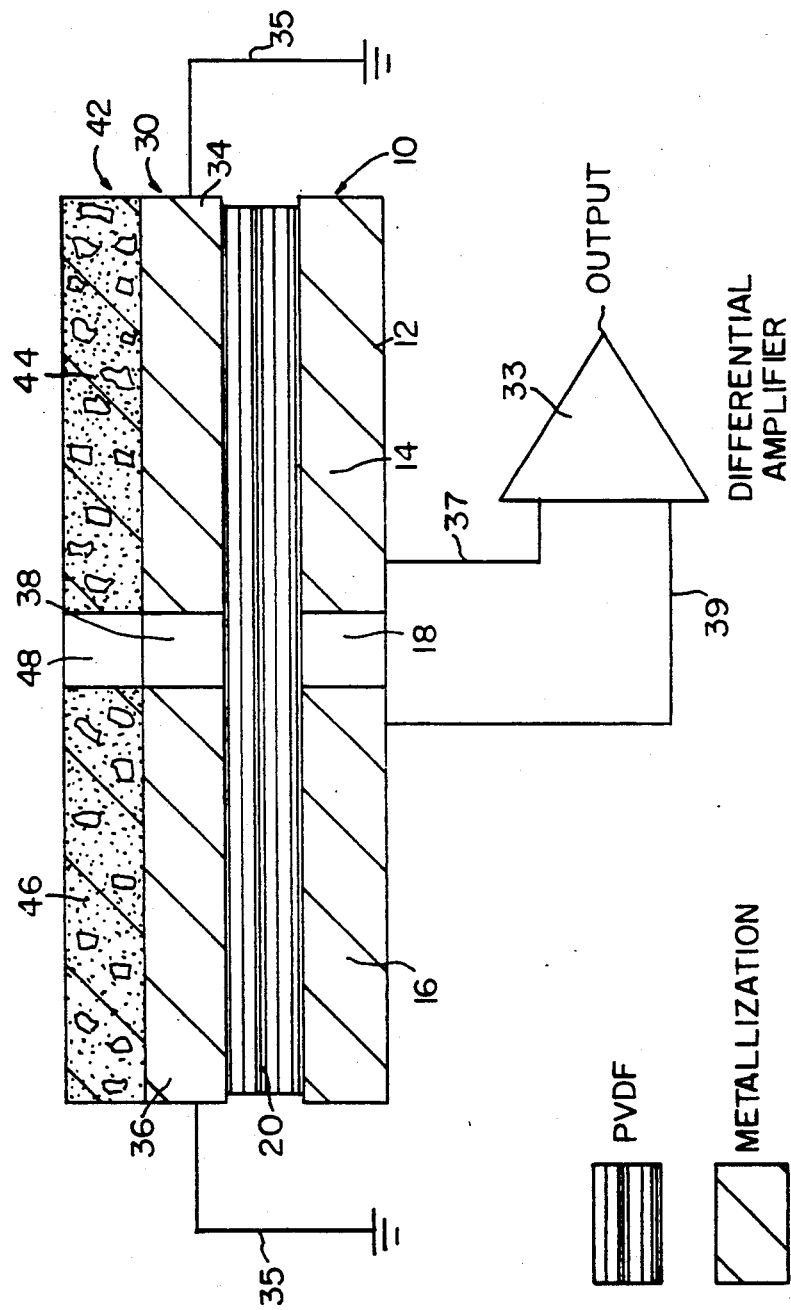
FIG. 1 is a side elevational view of the device of the present invention.

Referring now to FIG. 1 the device comprises a detector electrode 10 having two conductive areas 14 and 16 coated upon a non-conducting substrate 20 and separated from each other by a non-conducting gap 18. In the preferred mode illustrated in FIG. 2, the two electrode areas 14 and 16 are mutually interdigitated for reasons which will become apparent hereinbelow, sector 14 is designated as the specific detector segment and segment 16 as the non-specific detector segment. Specific electrode lead 37 connects segment 14 to differential amplifier 33 and non-specific electrode lead 39 connects segment 16 to the same differential amplifier 33 which in turn, is connected to a conventional output means.

An infrared transparent electrode (IRT electrode) 30 comprising conducting film segments 34 and 36 is placed on the second or upper surface of the pyroelectric film. When used in the active mode these segments may, but need not be infrared transparent, in the passive mode they must be infrared transparent. These segments are separated from each other by non conducting area 38. Ground electric lead 35 connects both said metallic segments 34 and 36 to ground.

Segment 34 is complementary to segment 14 and segment 36 is complementary to segment 16.

The heretofore described parts constitute the basic segments of the device. For the device to be operative, it must carry a reactant-reactive segment. A polymeric coupling base is provided upon the first or upper surface of the infrared transparent electrode segments 34 and 36. This polymeric base 42 comprises a reactant specific reagent segment 44 and a reactant non-specific reagent segment 46, separated by gap 48.

In the preferred embodiment, segment 44 is complementary to segment 14 and segment 46 is complementary to segment 16. That segment 44 overlying IRT electrode segment 34 carries a reagent reactant specific for the antigen sought to be detected and sector 46 overlying IRT electrode segment 36 carries a reactant non-specific reagent.

DESCRIPTION OF THE PREFERRED EMBODIMENTS

Figures 4, 5:
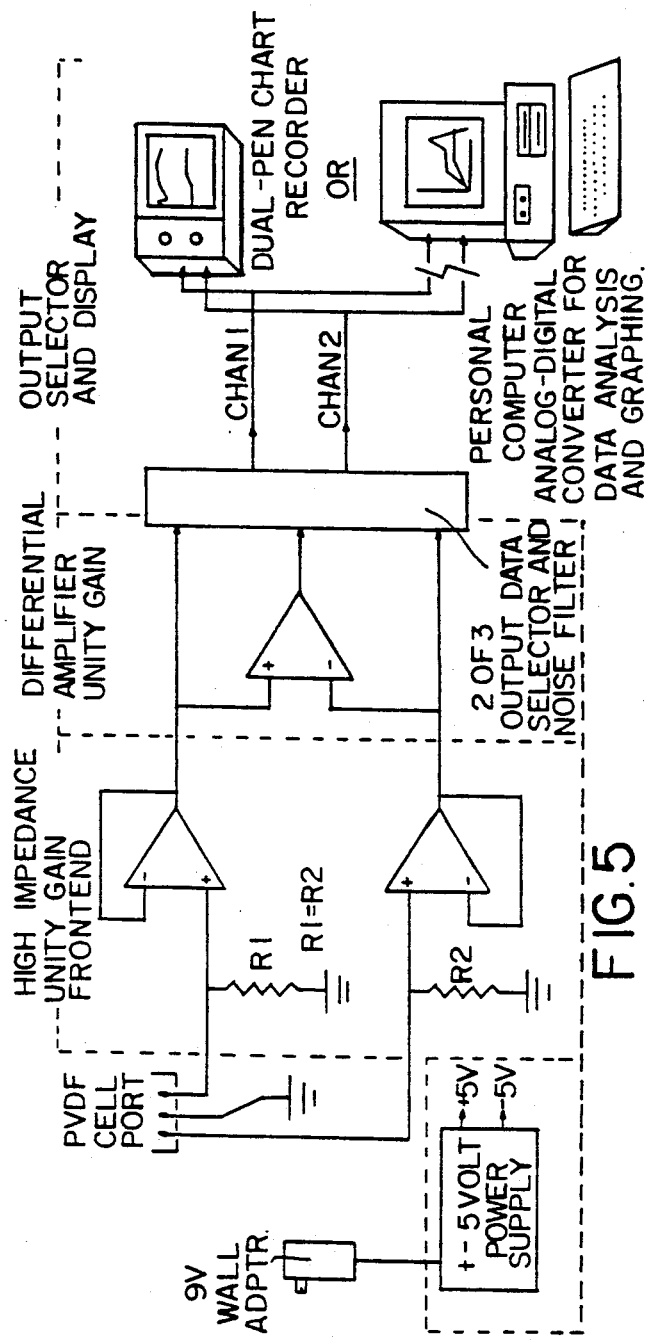
FIG. 4 is a exploded cross sectional view of a cell containing the device of the present invention.
FIG. 5 is a schematic diagram of the amplifying and output means utilized with the device.

FIG. 4 illustrates a sensor of FIG. 1 in its operating environment, that is to say, an assay sensor cell. In this cell, there is provided a base assembly 70 having contact means 75, 77 and 79, mounted therein, the upper ends of said contact means being electrically contactable with electro-conductive areas on the reverse side of the sensor disk and the other ends thereof being formed, suitably, as electrode pins and insertable into a base retention means 80. Specifically connects outer rim contact 75 to lead 35, contact 77 connects with lead 37 and contact 79 connects with lead 39. There is provided a sample well 60 having a reservoir 66 therein and a lower end 64 adapted to contact and form an electrical lead 35 and liquid, leak-proof seal with the obverse surface of the sensor. The opening in lower end 64 being of sufficient size to encompass at least a portion, suitably a major portion of the obverse surface above the electro-conductive means on the reverse side of the disk. Suitably, a screw thread 63 is provided on the outside of the lower portion of sample well 60, sized to interact with a similar screw thread on base retention unit 80, so that when the base assembly 70 is inserted into base retention unit 60, sensor 10 placed on said base assembly 70 and sample well 60, placed upon said sensor and screwed into base retention unit 60, the aforesaid leak-proof seal and electrical contacts are secured.

a) Formation of Active Layer

In the formation of the detector device 10, IRT electrode 30, initially comprises conventionally produced metal film upon the pyroelectric film 20. The areas which are to be retained as metal are then masked and the gap in between, namely gap 38 is etched out in a conventional manner. After the coating step discussed below, segments 34 and 36 are electrically connected and remain so during operation of the device.

As metal coatings there may be employed palladium, nickel, nickel/aluminum alloy, aluminum, copper, copper/nickel, silver, indium tin oxide. Some of these metals are more transparent to near IR than others, but all are partially transmitting at the thicknesses used; generally between 200 and 700 angstroms.

Each metal will have a characteristic redox potential in the various monomer solutions that can be used in electro-polymerization and however the optimal potential for polymerization will vary since over-voltage can result in the oxidation and thus degradation of the metal film.

In certain applications of this invention the metal is converted to metal oxides; these often form spontaneously depend on the metal. For example: silver, nickel, aluminum and indium tin oxide which is intrinsically an oxide metal film. Oxide formation can be accelerated by immersion in dilute alkali such as NaOH.

Oxides are subsequently coupled to by "coating" in silanes; specifically : aminopropyltriethoxysilane this provides for amino groups to which subsequent coupling reactions can be made for protein immobilization using for example p-benzoquinone as a bifunctional coupling reagent.

There are different ways of placing the reactant specific and reactant non-specific coatings upon the metal portion of the IRT electrode. Among these modes which are merely illustrative but not limiting, may be mentioned the following procedures.

In one mode, electrode portion 34 is connected to the negative pole of a low voltage direct current and segment 36 similarly connected to the positive pole of said source. The entire segment 30 is immersed in an electrically conductive solution of a suitable monomer and a reactant specific reagent nucleophilically, coupleable therewith. The action of the electric current polymerizes the monomer to provide a polymer layer 44 having the reagent linked thereto, said complex being coated specifically onto the metallic area 34 of IRT element 30. The IRT electrode 30 is then removed from that particular solution and placed in another solution of monomer and a reactant non-specific reagent nucleophilically, coupleable therewith.

The polarity is now reversed so that segment 34 is now connected to the positive pole and segment 46 to the negative pole. Thus, in similar manner, the appropriate coating 36 is placed upon segment 36. As monomers there may be employed: 1,3 phenylenediamine, 1,4 phenylenediamine, p-aminobenzoic acid, p-aminophenol and hydroxybenzyl alcohols In another coating embodiment, a polymeric base is coated, first upon segment 34 and then the appropriate antigen is coupled thereto by conventional coupling procedures, thereafter, segment 36 is similarly coated, first with the polymeric base and the reactant non-specific reagent is then coupled thereto to provide segment 46. These polymeric bases are usually epoxy/polyamine mixtures which are commercially available. Amines for epoxy polymers are generally proprietary blends of various polyamines such as those made by Henkel Corporation of Kankakee, Ill. which include the Gentamide which is an amido amine and the Versamine which is a ketimine; i.e. a protected amide that hydrolyzes on exposure to moisture to form an amine.

In a third modification, the polymeric coating is placed over the entire surface of the IRT electrode and by appropriate masking and irradiation, the reactant-reactive reagent is coupled to the portion overlying sector 34 to provide segment 44 and similarly, the reactant non-specific coating is coupled to the sector overlying segment 36 to provide segment 46.

There is no known limitation to the materials which can be used as reagents provided that these are coupleable and stable in the conditions of the various reactions. Of particular interest and value however are proteins, including enzymes. Generally any enzyme that reacts with or forms a product of some analytical interest with the evolution of heat; i.e. exothermic. Specifically, there may be named: glucose oxidase, alcohol oxidase, cholesterol oxidase, catalase, urease, peroxidase, cholesterol esterase etc.

Other proteins generally of interest are those which are immuno-specific binding proteins such as antibodies of all classes (IgG, IgM, IgE, etc.). Specific binding proteins such as avidin, isolated and purified cell surface receptors, etc.

EXAMPLE 1

Preparation of Interdigitated Electrodes

A sample of nickel coated Piezofilm (T.M.) a polyvinylidene fluoride polymer film that has been poled so that it is pyroelectric was spray coated on both sides with a positive acting photoresist to a thickness of about 1 to 2 microns, and then exposed to ultraviolet light (300 watts at a distance of about 10 cm) through a mask to provide a pattern of interdigitated alternating nickel electrodes, identical on both sides of the films such as shown in FIGS. 1-3. After exposure, the exposed resist is developed in a proprietary solution of alkaline phosphate salts (Microposit T. M. Developer CD-30 manufactured by Shipley Co Inc, Newton Mass.) and the nickel is etched from the PVDF film with a solution of ferric chloride (600 grams per liter in distilled $H_2O$; room temperature for 5 to 10 minutes ), leaving the desired pattern. The remaining resist is then removed from the nickel electrode patterns with the same solvent.

EXAMPLE 2

Preparation of Epoxy Coating on the Interdigitated Electrodes

The patterned electrode PVDF film produced in the previous example was then coated, on one side, with an epoxy resin mixture (Dow 324 2 ml of stock diluted 50% with xylene with Gentamide (0.5 ml) and Versamine (0.5 ml) cross-linking resins and DMP-30 accelerator (120 mg), in a total of 6.25 ml (Q.S. with xylene)) by spin coating so that a thin uniform film (ca 0.02 mm) covered the electrode patterned PVDF. After curing the epoxy resin by heating under an IR lamp of 200 watts at 30 cm for 40 minutes, the surface was further modified by contacting a solution of succinimidyl aryl nitrene (such as N-5-azido-2-nitrobenzoyloxysuccinimide) (5 mg in 100 ml of 0.01M carbonate buffer pH 9.2) to the epoxy surface film in the dark for 16 hours at room temperature. This reagent reacts with the excess, uncross-linked amines in the almost cured epoxy resin. The film is them washed with saline solution.

EXAMPLE 3

Coating of Electrodes with Specific and Non-specific Reagents

The epoxy surface coated electrodes produced in Example 2 were then placed in a shallow tray, an aqueous solution of glucose oxidase (20 ug/ml) was then filled into the tray to cover the electrodes which were then exposed to a source of ultraviolet light (300 watts at 10 cm for nominally 1 to 5 seconds (flashed) that was focused through a mask that allowed one nickel electrode pattern area to be irradiated, thus lysing the aryl nitrene which thus coupled the glucose oxidase to the selected surface of the epoxy film. The excess enzyme solution was washed off the film in the dark and replaced with a solution of bovine serum albumin (20 ug/ml) and the entire surface again similarly irradiated with a source of UV. The film was again washed to remove excess protein solution.

EXAMPLE 4

Mounting Device in Cell

The resulting differentially immobilized enzyme electrode film produced in the previous example was mounted in a suitable holder (FIG. 4) that electrically connected the electrode nickel under the epoxy film to a common circuit (at electrical ground), whereas the opposite nickel film surface, having been similarly etched (but not coated) with the identical electrode pattern was connected to separate electrodes. The resulting three electrode device was connected to the input of a high impedance differential amplifier circuit.

EXAMPLE 5

Operation of the Device

When the differentially immobilized glucose oxidase epoxy nickel film PVDF composite of Example 4 was exposed to an aqueous solution containing glucose (20 ug/ml), the glucose oxidase reaction, at the surface of the composite film electrode element produced heat that was proportional to the concentration of the substrate glucose.

EXAMPLE 6

Reagent Coating by Electropolymerization

A palladium coated sample of pyroelectric PVDF film was prepared in accordance with Example 1 to the specific electrode pattern by using a similar photoresist, exposing and developing in a similar manner. The exposed areas of the palladium were removed from the PVDF film by chemical etching in an acid solution comprised of 45% HCl and 5% Nitric acid for 5 minutes to remove unprotected palladium film. The enzymes glucose oxidase and catalase were then differentially immobilized to one side of the pair of palladium electrode by electropolymerization.

A grid of nickel chromium wire (4"×4", 24 gauge, 16 mesh) was used as the working cathode, and placed 1-2 cm from the surface of the specific palladium electrode which was connected to the anode, all other palladium electrodes being connected to the cathode side of the circuit. The reference electrode is a standard Calomel electrode. A potentiostat was used to maintain a constant electrode potential during the polymerization process The monomer solution of 0.363 grams of 1,3 phenylenediamine di-hydrochloride, 1.3 grams of ammonium hydrogen phosphate, 0.1 grams of polyvinylpyrrolidone was adjusted to pH 9.0 with NaOH and the total volume adjusted to 100 ml with deionized water. To this solution, 1 milligram of the enzyme glucose oxidase (E.C. 1.1.3.4.) in 100 ul of 0.15M NaCl was added together with 0.02 milligram of the enzyme catalase (E.C. 1.11.1.6) in 20 ul of 0.15M NaCl. The working electrode potential was adjusted to +0.600 volts with respect to the Calomel reference electrode and the suitably connected palladium-PVDF sample placed into the monomer solution. The measured current varied with absolute electrode area and monomer solution and was seen to fall rapidly from its initial value. After 30 to 40 minutes, a suitable protein crosslinked polymer was formed on the anode metallization. A uniformly reflecting coat, yellow-gold in appearance could be seen.

The palladium-PVDF sample was removed from the monomer bath and thoroughly rinsed in deionized water. The electrode now specifically coated with the two enzymes was reconnected to the cathode or left unconnected and the previously uncoated reference electrode reconnected as the anode. The palladium-PVDF film was reimmersed in a monomer solution that is identical to the first solution except that the enzymes glucose oxidase and catalase had been replaced by 1 milligram of bovine serum albumin. The reference electrode was then polymerized for 30 to 40 minutes until a uniform polymer coating was achieved. The sample was again removed from the monomer bath and thoroughly rinsed in deionized water followed by a rinse in 10% glycerol in 0.15M NaCl solution and subsequently air dried at room temperature.

The thus produced differentially electrochemical immobilized enzyme palladium-PVDF film is subsequently mounted in a suitable holder (as in Example 4). On exposure to a liquid medium containing a given concentration of glucose (whole blood) (as in Example 5), results were obtained which are shown in Table I.

Table I

The differential pyroelectric response is a voltage produced across a load as a result of the charge output from the device; this is a function of the rate of change of temperature with time. The output is best evaluated as the integration of the output voltage response over a given time interval. For glucose oxidase immobilized films, the output is integrated for 30 seconds around the peak voltage output from −5 seconds to +25 seconds (30 seconds total)

| Glucose concentration | peak voltage (mvolts) (into a 10e10 ohm load) | integrated voltage volts/sec$^2$ |
| --- | --- | --- |
| 50 mg % | 1.9 mv | 23 mv/sec$^2$ |
| 100 mg % | 4.8 mv | 48 mv/sec$^2$ |
| 250 mg % | 17 mv | 141 mv/sec$^2$ |

Output will vary as a function of electrode surface area, enzyme loading, electro-polymer type as well as the load impedance of the device. These results were obtained with the same device.

EXAMPLE 7

Alternate Enzymatic Coupling

A palladium coated pyroelectric-PVDF film sample is prepared as in Example 6. The enzyme glucose oxidase is replaced by an similar concentration of the enzyme cholesterol oxidase (E.C. 1.1.3.6) in the monomer solution and is immobilized by co-electropolymerization onto the appropriate electrode area.

EXAMPLE 8

Antibody Antigen Testing

A palladium coated sample of pyroelectric PVDF film is prepared in accordance with the procedures of Example 5. An antibody protein specifically prepared against antigens present on the bacterium Streptococcus type strain A, as a polyclonal from the immunization of rabbits and further purified by techniques and methods well known to the art. The purified antibody, as a rabbit IgG is differentially immobilized to one side of the pair of palladium electrodes by electropolymerization as in Example 5. 1 milligram of the anti-Streptococcus A IgG in 100 ul of 0.15M NaCl is added to the monomer solution. Similarly the palladium-PVDF film is reimmersed in a monomer solution that is identical to the first solution except that the anti-Streptococcus A antibody is again replaced by a similar solution of non-specific rabbit IgG.

EXAMPLE 9

Infra-red Pulse Conductivity Measurement

In this method, the electrode elements are evaluated by irradiating the surface of the electrode elements with a source of near infrared radiation (904 nanometers). Using a laser diode (8 watts peak output manufacture by RCA) a series of IR pulses (ca 280 per second) are controlled so that, by conversion to thermal energy at the surface of the film, the pyroelectric output is recorded as a maximum output from each element of the pair, and being matched in thermal properties, the differential output is recorded as a minimum. This is done by measuring the amplitude of the on-off peaks generated in response to the laser energy. Typical results are given in Table II.

Table II

Pulsed IR Thermal Conductivity 8 watts at 904 nm; 200 nanosecond pulse width nominal 170 pulses for 600 milliseconds repeated at 2.5 second intervals. Output is peak voltage response of integrated thermal response over each 2.5 second interval.

| Analyte (Sample) | peak voltage (1 cycle) | mean peak voltage (25 cycles) | S.D. % |
| --- | --- | --- | --- |
| Device #1 | | | |
| buffer (zero or baseline control) | 0.323 mv | 0.325 mv | 4.6% |
| biotinylated IgG 250 nanograms/ml | 0.400 mv | 0.400 mv | 2.5% |
| Device #2 | | | |
| buffer (zero or baseline control) | 0.277 mv | 0.281 mv | 3.3% |
| biotinylated IgG 25 nanograms | 0.312 mv | 0.313 mv | 6.2% |

Correlation of device to device response in a quantitative manner requires controlled electropolymerization of the primary binding protein to each electrode area.

EXAMPLE 10

Monoclonal Antibodies

The procedures of example 8 were repeated, but in place of the rabbit IgG there was utilized a cocktail of antibody proteins to the various and multiple antigens found on the various species and subspecies and specifically prepared against those antigens present on the bacterium Salmonella enteriditis, prepared as monoclonals, isolated, cloned and produced by techniques and methods well known to the art. The reference electrode is suitably electro-polymerized with a similar non-specific monoclonal antibody of the same class, such as a mouse monoclonal IgG which is non-specific. Again, the electrode elements are evaluated by irradiating the surface of the electrode elements with a source of near infrared radiation using a laser diode as in Example 10.

I claim:

1. A device for detecting the presence of a predetermined reactant in a fluid suspected of containing the same which comprises:
   a pyroelectric film having a first and a second surface,
   a first electrode in contact with a portion of the first surface of said pyroelectric film
   a second electrode in contact with a portion of the first surface of said pyroelectric film,
   said first and said second electrodes being proximate to but electrically insulated from each other,
   an infra-red transparent third electrode having a first and second surface, said first surface being in contact with the second surface of said film.

2. A device of claim 1 wherein the surface areas of said first and said second electrodes are substantially equal.

3. A device of claim 2 wherein the said first and second electrodes are interdigitated.

4. A device of claim 1 further comprising
   a first coating containing a non specific reagent placed on said second surface of said third electrode and
   a second coating containing a reagent specific to said predetermined reactant placed upon the second surface of said third electrode adjacent to said first coating.

5. A device of claim 4 wherein the said first coating is substantially complementary in surface area, outline and location to those of the first electrode and
   the said second coating is substantially complementary in surface area, outline and location to those of the second electrode.

6. A device of claim 5 wherein said first and second coatings comprise a layer of polymer having the appropriate reagent chemically bonded thereto.

7. A device of claim 6 wherein the polymer is a substantially water insoluble polymer.

8. A device of claim 6 wherein the polymer is derived from a monomer bonded to said reagent prior to polymerization.

9. A device of claim 6 wherein the polymer is bonded to said reagent subsequent to polymerization.

10. A device of claim 5 wherein the reagent is bonded directly to the second surface of said third electrode.

11. A device of claim 5 wherein the second surface of said third electrode is activated prior to bonding the reagent thereto.

12. A device of claim 11 wherein the electrode surface is a metal oxide.

13. A device of claim 4 wherein the reagent is a reagent capable of participating in an exothermic reaction with said predetermined reactant.

14. A device of claim 4 wherein the reagent is a reagent capable of participating in an endothermic reaction with said predetermined reactant.

15. A device of claim 4 wherein the reagent is a reagent capable of participating in a coupling reaction with said predetermined reactant.

16. A device of claim 4 wherein the reagent is selected from the group consisting of enzymes, monoclonal antibodies, polyclonal antibodies and antigens, generally, of any substance or compound that is capable of eliciting an immune response by the formation of specific antibodies in the appropriate condition.

17. A device of claim 5 further comprising:
    means for connecting said third electrode to ground,
    means for detecting electrical signals from said first and said second electrodes,
    means for amplifying the signals from said first and said second electrodes,
    means for comparing the said amplified signals from said first and said second electrodes.

18. A device of claim 17 wherein the means for detecting, means for amplifying and means for comparing signals from said differential amplifier are a differential amplifier.

19. A device of claim 18 additionally comprising a means for recording signals from said differential amplifier.

20. A method for detecting the presence of a predetermined reactant in a fluid suspected of containing the same utilizing a device of claim 17 which comprises: contacting the said first and second coatings of said third electrode with said fluid and measuring the differential signals generated by said first and said second electrodes.

21. A method for quantitatively detecting the presence of a predetermined reactant in a fluid suspected of containing the same utilizing a device of claim 17 which comprises:
    contacting the said first and second coatings of said third electrode with said fluid and measuring the differential signals generated by said first and said second electrodes, and comparing said measurements to predetermined standards.

22. A method for detecting the presence of a predetermined reactant in a fluid suspected of containing the same utilizing a device of claim 17 which comprises:
    contacting the said first and second coatings of said third electrode with said fluid,
    removing excess fluid,
    irradiating said first and second coatings with infrared radiation,
    and measuring the differential signals generated by said first and said second electrodes.

23. A method of claim 22 wherein the irradiation comprises application of pulses of predetermined intensity from a uniform, controlled source of thermal radiation capable of eliciting a pyroelectric response by the film.

24. A method of claim 23 wherein said pulses are applied at predetermined time intervals.

25. In the process of making a device of claim 5, the stage of applying the said first and said second coatings to provide a device of claim 5 which comprises the steps of:

separating said third electrode into first and second thermally and electrically mutually non contacting segments, connecting said first segment which is complementary to said first electrode to a negative pole of a source of low voltage direct current, connecting said second segment which is complementary to said second electrode to a positive pole of said source of low voltage direct current, immersing at least said two segments of said third electrode in an electrically conductive solution of monomer and reactant specific reagent nucleophilically coupleable therewith, whereby said monomer is polymerized and linked to said second segment and said reagent is coupled to said polymer, connecting said first segment which is complementary to said first electrode to a positive pole of a source of low voltage direct current, connecting said second segment which is complementary to said second electrode to a negative pole of said source of low voltage direct current, immersing at least said two segments of said third electrode in an electro-conductive solution of monomer and reactant non-specific reagent nucleophilically coupleable therewith, whereby said monomer is polymerized and linked to said second segment and said reactant non-specific reagent is coupled to said polymer and electrically connecting said first segment to said second segment of said third electrode.

26. A process of claim 25 wherein the separation of the two segments of the third electrode is achieved by etching thereon a pattern complementary to the pattern of said first and said second electrode.

27. In the process of making a device of claim 5, the stage of applying the said first and said second coatings to provide a device of claim 5 which comprises the steps of:

separating said third electrode into first and second thermally and electrically mutually non contacting segments, connecting said first segment which is complementary to said first electrode to a negative pole of a source of low voltage direct current, connecting said second segment which is complementary to said second electrode to a positive pole of said source of low voltage direct current, immersing at least said two segments of said third electrode in an electro-conductive solution of monomer having reactant specific reagent coupled thereto, whereby said monomer is polymerized and linked to said second segment and having said reagent coupled thereto, connecting said first segment which is complementary to said first electrode to a positive pole of a source of low voltage direct current connecting said second segment which is complementary to said second electrode to a negative pole of said source of low voltage direct current, immersing at least said two segments of said third electrode in a mixture of monomer and having reactant non-specific reagent coupled thereto and whereby said monomer is polymerized and linked to said second segment having said reactant non-specific reagent coupled thereto, electrically connecting said first segment to said second segment of said third electrode.

28. A process of claim 27 wherein the separation of the two segments of the third electrode is achieved by etching thereon a pattern complementary to the pattern of said first and said second electrode.

29. In the process of making a device of claim 5, the stage of applying the said first and said second coatings to provide a device of claim 5 which comprises the steps of:

separating said third electrode into first and second thermally and electrically mutually non contacting segments, connecting said first segment which is complementary to said first electrode to a negative pole of a source of low voltage direct current, connecting said second segment which is complementary to said second electrode to a positive pole of said source of low voltage direct current, immersing at least said two segments of said third electrode in an electro-conductive solution of monomer, whereby said monomer is polymerized and linked to said second segment and then coupling said reactant specific reagent to said polymer, connecting said first segment which is complementary to said first electrode to a positive pole of a source of low voltage direct current, connecting said second segment which is complementary to said second electrode to a negative pole of said source of low voltage direct current, immersing at least said two segments of said third electrode in an electro-conductive solution of monomer, whereby said monomer is polymerized and linked to said second segment and then coupling said reactant non-specific reagent to said polymer and electrically connecting said first segment to said second segment of said third electrode.

30. A process of claim 29 wherein the separation of the two segments of the third electrode is achieved by etching thereon a pattern complementary to the pattern of said first and said second electrode.

* * * * *